United States Patent [19]
Bauer et al.

[11] Patent Number: 5,597,466
[45] Date of Patent: Jan. 28, 1997

[54] PREPARATION OF SUBSTANTIALLY SALT-FREE AQUEOUS SOLUTIONS OF BISAMINOXYALKANES

[75] Inventors: Gerhard Bauer, Weinheim; Roland Baumstark, Neustadt; Kaspar Bott, Mannheim; Hartwig Voss, Frankenthal, all of Germany

[73] Assignee: BASF Aktiengesellschaft, Ludwigshafen, Germany

[21] Appl. No.: 279,888

[22] Filed: Jul. 26, 1994

[30] Foreign Application Priority Data

Jul. 29, 1993 [DE] Germany .......................... 43 25 455.1

[51] Int. Cl.$^6$ ...................................... B65D 83/04
[52] U.S. Cl. .................. 204/529; 204/530; 564/253; 564/256; 564/301
[58] Field of Search .................... 252/182.23; 523/310; 564/253, 256, 297, 298, 300, 301; 525/382; 204/529, 530

[56] References Cited

U.S. PATENT DOCUMENTS

| 3,247,243 | 4/1966 | Villani | 564/301 X |
| 5,393,921 | 2/1995 | Lazar | 564/301 X |

FOREIGN PATENT DOCUMENTS

| 0516074 | 12/1992 | European Pat. Off. . |
| 4117487 | 12/1992 | Germany . |
| 4219384 | 12/1993 | Germany . |
| WO93/25588 | 12/1993 | WIPO . |

OTHER PUBLICATIONS

*Some Alkoxy– and Alkylenedioxydi–amines and Alkoxy– and Alkylenedioxydi–guanidines.* By A. T. Fuller and Harold King. pp. 963–969 (1947).
*S–[W–(Aminooxy)alkyl]isothiuronium Salts, W,W'–Bis(aminooxy)alkanes and Related Compounds1* By Ludwig Bauer and K. S. Suresh. vol. 28, pp. 1604–1608 (1963).

*Primary Examiner*—Judy M. Reddick
*Attorney, Agent, or Firm*—Oblon, Spivak, McClelland, Maier & Neustadt, P.C.

[57] ABSTRACT

Salt-free aqueous solutions of bisaminoxyalkanes (I) are prepared by a process in which a) a dihaloalkane (II) is converted with a ketoxime (III) in an aqueous solution of a strong mineral base into the alkylene bisoxime ether (IV), b) the alkylene bisoxime ether (IV) is cleaved with a strong mineral acid and water to give the ketone and the salt of the mineral acid with the bisaminoxyalkane (I), and the ketone is separated off in a conventional manner, c) an alkali metal hydroxide is added to the remaining aqueous solution to liberate the bisaminoxyalkane (I) and d) the ionic components are removed from the resulting aqueous solution by electrodialysis.

9 Claims, No Drawings

PREPARATION OF SUBSTANTIALLY SALT-FREE AQUEOUS SOLUTIONS OF BISAMINOXYALKANES

The present invention relates to a novel process for the preparation of substantially salt-free solutions of bisaminoxyalkanes (I).

The present invention furthermore relates to dispersions of crosslinkable polymers and the free bases I as crosslinking agents, which dispersions have a low salt content, and to specific steps of the overall process.

Bisaminoxyalkanes (I) are generally known and serve as crosslinking agents for dispersions of addition polymers, polycondensates or polyadducts which contain reactive carbonyl groups in the molecule (cf. DE-A 41 17 487 or the earlier German Application P 42 19 384.2).

The preparation of bisaminoxyalkanes (I) reacting N-protected hydroxylamines with dihaloalkanes (II) and then eliminating the protective groups from the hydroxylamine nitrogen is the most important process industrially.

J. Chem. Soc. (1947), 963 discloses the reaction of N-hydroxyurethanes as N-protected hydroxylamines, and J. Org. Chem. 28 (1963), 1604 describes the use of N-hydroxyphthalimide for this purpose.

However, owing to the low yields and the losses of the compound containing the protective group, these synthesis methods are unsatisfactory.

Furthermore, the bisaminoxyalkanes (I) are obtained in protonated form, and technical difficulties are encountered in recovering them as aqueous solutions of the free bases I, since an aqueous mixture of the free bases I and the salts is formed in the neutralization step required for this purpose.

However, since the salt content of the bisaminoxyalkanes (I) may lead to coagulation of the relevant dispersions when said bisaminoxyalkanes are used as crosslinking agents, it is an object of the present invention to provide a process for the preparation of substantially salt-free aqueous solutions of bisaminoxyalkanes (I) and dispersions of crosslinkable polymers which contain these products.

We have found that this object is achieved by a process for the preparation of substantially salt-free aqueous solutions of bisaminoxyalkanes (I), wherein a) a dihaloalkane (II) is converted with a ketoxime (III) in an aqueous solution of a strong mineral base into the alkylene bisoxime ether (IV), b) the alkylene bisoxime ether (IV) is cleaved with a strong mineral acid and water to give the ketone and the salt of the mineral acid with the bisaminoxyalkane (I), and the ketone is separated off in a conventional manner, c) an alkali metal hydroxide is added to the remaining aqueous solution to liberate the bisaminoxyalkane (I) and d) the ionic components are removed from the resulting aqueous solution by electrodialysis.

We have also found substantially salt-free polymer dispersions which contain the compound (I). The present invention also relates to particularly advantageous embodiments of certain stages of the overall process.

The novel process can be illustrated as follows in a simple case:

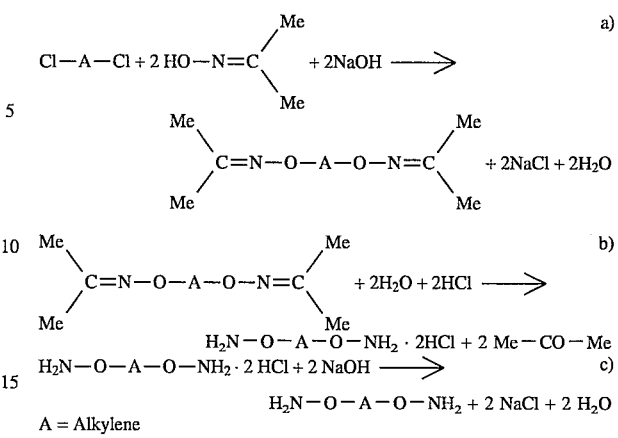

d) Electrodialysis of the aqueous product solutions from stage c) for the substantial removal of sodium chloride.

Stages a) to c) can be carried out in a conventional manner. Particularly advantageous novel embodiments are described further below.

Preferred products of the process are those which are derived from straight-chain $C_2$–$C_{12}$-alkanes, in particular from butane. Suitable corresponding dihaloalkanes (II) are primarily the α,ω-dichloro and the α,ω-dibromo compounds.

Particularly suitable ketoximes (III) are those of the formula

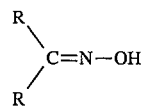

where the radicals R are identical or different and are each a $C_1$–$C_{10}$ organic radical, preferably $C_1$–$C_4$-alkyl, such as n-propyl, isopropyl, n-butyl, tert-butyl or especially methyl or ethyl, acetone oxime being a particularly preferred ketoxime (III).

The ketoximes (III) are known or can be obtained by known methods, for example by reacting the corresponding ketones with hydroxylamine.

The molar ratio of ketoxime (III) to dihaloalkane (II) is preferably from 2:1 to 3:1, in particular from 2:1 to 2.2:1.

Suitable aqueous solutions of a strong mineral base are aqueous alkali metal or alkaline earth metal hydroxide solutions, sodium hydroxide and calcium hydroxide being preferred for economic reasons. The sparingly soluble alkaline earth metal hydroxides may also be used in the form of their suspension. Advantageously from 1 to 2, in particular from 1 to 1.5, equivalents of the hydroxide are used per mol of ketoxime (III).

In order to achieve satisfactory yields, it is generally necessary to carry out the reaction of dihaloalkanes (II) with the ketoximes (III) in a solvent, water-soluble solvents, for example dimethylformamide or dimethyl sulfoxide, being preferred since they ensure sufficient solubility of the polar reactants in the organic phase.

However, it was found that the presence of a phase transfer catalyst makes the use of a solvent entirely or substantially superfluous.

The phase transfer catalysts used may be quaternary ammonium or phosphonium salts, preferably tetraalkylammonium, trialkylbenzylammonium, tetraalkylphosphonium or trialkylbenzylphosphonium salts. The triethyl-, tributylbenzyl- and tetrabutylammonium chlorides, bromides and hydrogen sulfates and tributylhexadecylphosphonium bromide are particularly preferred.

The phase transfer catalyst is used, as a rule, in amounts of from 0.5 to 2, preferably from 0.7 to 1, mol %, based on the ketoxime (III).

In the case of acetone oxime, it was found that the reaction takes place particularly readily with a phase transfer catalyst alone and without the presence of significant amounts of a solvent. This embodiment is particularly preferred by itself and as part of the overall process, because it dispenses with the technical complication due to the solvent.

The reaction of dihaloalkanes (II) with the ketoximes (III) is usually carried out at from 40° to 120° C., in general from 60° to 105° C., and at from 0.5 to 2 bar, preferably at atmospheric pressure.

The reaction times are usually from 1 to 10, in general however from 4 to 5, hours.

The process is carried out, as a rule, by heating the dihaloalkane (II), the aqueous strong mineral base and the phase transfer catalyst and, if required, the solvent to the reaction temperature and then metering in the ketoxime (III).

A salt-containing aqueous phase and an organic phase which consists of the alkylene bisoxime ether (IV) or contains the latter are obtained in the reaction. The organic phase, if necessary after removal of the organic solvent, may be used in this form in the next process stage, in which the alkylene bisoxime ether (IV) is cleaved with an aqueous strong mineral acid to give the salt of the mineral acid with the bisaminoxyalkane (I) and the ketone.

Mineral acids suitable for this reaction are sulfuric acid, nitric acid, phosphoric acid and in particular hydrochloric acid, preferably in aqueous solution.

These strong mineral acids are used, as a rule, in a molar ratio of from 2:1 to 6:1, advantageously from 2:1 to 4:1, based on the alkylene bisoxime ether (IV).

The cleavage of the alkylene bisoxime ether (IV) is generally carried out at from 80° to 110° C. and from 0.5 to 1.5, preferably from 0.7 to 1, bar. Reaction times are usually from 2 to 10, in particular from 3 to 5, hours.

In a preferred embodiment of the novel process, which is also particularly advantageous by itself, alkylene bisacetone oxime ethers are used as starting materials and are hydrolyzed with aqueous hydrochloric acid. The acetone formed is removed continuously from the reaction mixture, and some of the hydrogen chloride and water may pass over simultaneously.

In this case, working up is carried out by completely removing hydrogen chloride and water which remain in the reaction vessel, advantageously with the aid of an entraining agent, taking up the remaining salt of the mineral acid with the bisaminoxyalkane (I) in water and separating off the entraining agent.

Suitable entraining agents are benzene, carbon tetrachloride and especially cyclohexane.

An alkali metal hydroxide is added to the remaining aqueous salt solution in order to liberate the bisaminoxyalkane (I), particularly preferred alkali metal hydroxides being potassium hydroxide and sodium hydroxide.

With regard to the electrodialysis to be carried out according to the invention in the subsequent process stage, the liberation of the bisaminoxyalkane (I) is usually carried out using the stoichiometric or slightly superstoichiometric amounts, based on the amount of the I salt, of an alkali metal hydroxide, in order thus to avoid unnecessarily increasing the electrolyte content of the solution.

The neutralization is carried out in a conventional manner and therefore requires no further explanations.

After the neutralization with the alkali metal hydroxide, the aqueous solution containing the bisaminoxyalkane (I) and the alkali metal salt is subjected, according to the invention, to electrodialysis in order to separate off the ionic components.

The removal of salts from aqueous salt solutions by means of electrodialysis and corresponding electrodialysis apparatuses are known in principle and are described, for example, in H. Strathmann, Trennung von molekularen Mischungen mit Hilfe synthetischer Membranen, Steinkopf Verlag, Darmstadt, 1979, pages 76 to 86, and in D. S. Flett, Ion Exchange Membranes, Ellis Horwood, Chichester 1983, pages 179 to 191.

The salt removal step of the novel process is advantageously carried out by arranging anion and cation exchange membranes alternately and parallel to one another between two electrodes and sealing the chambers formed by inserted spacer frames from one another. An element consisting of a diluate chamber, a concentrate chamber and an anion and a cation exchange membrane is referred to as a repeating cell unit.

The salt-containing product solution (also referred to below as diluate) is passed through the chambers which are bounded in the direction of the anode by an anion exchange membrane. To take up the salt to be separated off, an aqueous electrolyte-containing solution (also referred to below as concentrate) whose initial conductivity is, for example, from 1 to 10 mS/cm is passed through the chambers which are bounded by a cation exchange membrane in the direction of the anode. The electrolyte used in the concentrate is, as a rule, the salt which is to be separated off from the diluate.

The cathode and anode spaces are separated from the diluate and concentrate chambers, respectively, by the last membrane in each case, preferably a cation exchange membrane. An electrolyte-containing solution is advantageously caused to flow through the electrode chambers during the electrodialysis process, in order to remove gases formed at the electrode chamber. Advantageously, a 1–10% strength by weight aqueous sodium sulfate solution is used for flushing the electrodes.

The ion exchange membranes used are commercial, anion-selective and cation-selective membranes. They generally have a permselectivity of more than 0.9 and an electrical resistance of less than 5 $\Omega cm^2$ (cf. Desalination 34 (1980), 77 to 95). The ion exchange membranes generally consist of a carrier film or a woven carrier fabric of a polyester, polyethylene or polyvinyl chloride, on which the prepared exchanger resins are applied, or on which the exchanger resin was first polymerized in a conventional manner and then further treated in order to obtain cation or anion exchangers (cf. Ullmanns Encyklopädie der technischen Chemie, 4th Edition, Volume 13, page 279 et seq. (1977)). Particular examples are strongly acidic cation exchangers or strongly basic anion exchangers based on crosslinked styrene/butadiene or styrene/divinylbenzene copolymers modified by sulfo or quaternary ammonium groups, on a woven polyvinyl chloride support fabric.

In the novel process, electrodialysis is carried out in general at below 100° C., preferably from 15° to 80° C., and at a current density which as a rule does not exceed 3,000 $A/m^2$ and is preferably from 10 to 1,000 $A/m^2$. The direct current voltage required for ion transport through the membranes depends on the type and concentration of the ions. Owing to the electrical resistance of the electrodialysis cell, voltages of up to 3 V per repeating cell unit are present at the abovementioned current densities. The membranes usually have a spacing of from 2.0 to 0.4 mm.

The novel process can be carried out both continuously in a plurality of membrane stacks connected in series and batchwise by circulating the liquid streams with the aid of buffer vessels or by mixed forms of these methods.

To enable the electrodialysis to be carried out without problems, it is advisable to bring the product solution to a pH which corresponds to the pH of the free bisaminoxyalkane (I) in aqueous solution or is up to about one unit higher.

Furthermore, oligomers which are formed during the cleavage of the alkylene bisoxime ether (IV) should be separated off. This can be effected by filtration after the aqueous solution of the salt of the mineral acid with bisaminoxyalkane (I) has been neutralized, since the byproducts are for the most part precipitated. To improve the separation, active carbon may be added before or after the precipitation.

The extent to which the concentration of the ionic components is decreased can be varied within wide limits. The relevant requirements, especially the time and current of the electrodialysis, depend essentially on the initial salt concentration in the diluate and on the current efficiency.

If the aqueous solutions of the bisaminoxyalkanes (I) are to be used as crosslinking agent-containing additives in the dispersions, the content of salts of mineral acids with alkali metals in the solution is reduced by electrodialysis to below 20, preferably below 10, mol %, based on the bisaminoxyalkane (I).

The reduction of the concentration of the ionic components in the aqueous solutions of the bisaminoxyalkanes (I) by electrodialysis is furthermore not related to the source of the solutions, ie. said reduction is suitable for removing salts from any aqueous solutions of bisaminoxyalkanes (I) and alkali metal salts.

The novel, substantially salt-free aqueous solutions of bisaminoxyalkanes (I) may be used directly as additives in aqueous dispersions of crosslinkable polymers which contain carbonyl groups as aldehyde or ketone functions in the molecule. Since they contain virtually no further salts, they can be added directly to the polymer dispersions without adversely affecting their colloidal stability, even in the case of systems labile in the presence of electrolytes.

Owing to the low salt content, clear films are obtained from the dispersions.

Suitable polymers are polycondensates or polyadducts which contain carbonyl groups as aldehyde or ketone functions. However, addition polymers of olefinically unsaturated compounds which have reactive carbonyl functional groups are preferred.

These addition polymers are obtained by copolymerization of monomers which contain a carbonyl group as an aldehyde or ketone function (monomers A) with other monomers (monomers B).

Suitable monomers A are acrolein, methacrolein, vinyl alkyl ketones and formylstyrenes, as well as alkyl acrylates or methacrylates or N-alkyl-substituted acrylamides or methacrylamides which contain a carbonyl group as an aldehyde or ketone function in the alkyl moiety.

2- (3-Oxobutyryloxy)-ethyl methacrylate (acetoacetoxyethyl methacrylate) and especially N-(1,1-dimethyl-3-oxobutyl)-acrylamide (diacetoneacrylamide) are particularly suitable.

Suitable monomers B are the esters of acrylic or methacrylic acid, preferably the alkylesters, the $C_1$–$C_{10}$alkyl esters, such as methyl acrylate, ethyl acrylate, n-butyl acrylate, 2-ethylhexyl acrylate and methyl methacrylate, and mixtures of these monomers being particularly preferred.

Other suitable monomers B are vinyl carboxylates, preferably of $C_1$–$C_{10}$-carboxylic acids, such as vinyl propionate or vinyl laurate, as well as vinylaromatics of up to 20 carbon atoms, preferably styrene, and olefinically unsaturated nitriles, vinyl halides or aliphatic $C_4$–$C_8$-hydrocarbons having at least two conjugated olefinic double bonds, in particular butadiene, isoprene chloroprene.

Methacrylamides, monomers having hydroxyl functional groups or monomers having salt-forming groups, in particular carboxyl groups, such as acrylic acid or methacrylic acid, are also suitable monomers B.

The polymers usually contain from 0.001 to 20, in particular from 0.01 to 10, especially from 0.05 to 5, % by weight of carbonyl groups as ketone or aldehyde functions. They may be prepared by mass or suspension polymerization but are preferably prepared by emulsion or solution polymerization.

The emulsion polymerization is used in particular for the preparation of aqueous primary dispersions. As a rule, the monomers are reacted with a water-soluble initiator in the presence of an emulsifier at from 30° to 90° C. in water.

Suitable initiators are, for example, sodium persulfate, potassium persulfate, ammonium persulfate, tert-butyl hydroperoxide and water-soluble azo compounds or redox initiators.

For example, alkali metal salts of relatively long-chain fatty acids and alkylsulfates, alkylsulfonates, alkylated arylsulfonates or alkylated diphenyl ether sulfonates may also be used as emulsifiers.

Other suitable emulsifiers are reaction products of alkylene oxides, in particular ethylene oxide or propylene oxide, with fatty alcohols, fatty acids, phenol or alkylphenols.

For aqueous secondary dispersions, the polymer is first prepared by solution polymerization or solution polycondensation in an organic solvent and then dispersed in water.

If the polymers contain highly hydrophilic groups, such as the carboxyl group, they are as a rule self-dispersing and the use of other emulsifiers which ere disadvantageous for some intended applications is therefore unnecessary.

A bisaminoxyalkane (I) in the form of a substantially salt-free aqueous solution is added to the dispersion for the purpose of crosslinking.

The crosslinking agent may be added to the dispersion in less than or more than the stoichiometric amount, preferably in the stoichiometric amount, based on the carbonyl groups to be crosslinked and present as ketone or aldehyde functions.

The dispersions may also contain further components, such as film forming assistants, fillers or fungicides.

The solids content of the novel dispersions is preferably from 20 to 90, in particular from 30 to 70, % by weight.

Otherwise, the preparation of such dispersions is familiar to the skilled worker (cf. the earlier German Application P 42 19 384.2), so that further explanations are unnecessary in this respect.

The novel dispersions are suitable, for example, as sealing compounds, adhesives and coating materials.

EXAMPLE 1

Preparation of butylene-1,4-bisacetone oxime ether (Stage a)

A mixture of 576 g (4.53 mol) of 1,4-dichlorobutane, 1,080 g of 50% strength (13.5 mol) sodium hydroxide solution, 270 g of water and 36 g of 50% strength (65 mmol) tetrabutylammonium chloride solution in water was heated to 50° C., and 657 g (9.00 mol) of acetone oxime were added in the course of one hour by the feed method. The mixture was refluxed for three hours, after which the precipitated sodium chloride was dissolved in 1,500 g of water and the phases were then separated. After distillation of the organic phase, the oxime ether was obtained in a yield of 65%.

EXAMPLE 2

Preparation of the hydrochloride of 1,4-bisaminoxybutane (Stage b)

500 g (2.5 mol) of butylene 1,4-bisacetone oxime ether and 1,000 g of water were heated to the boil and 1,000 g of concentrated (10 mol) hydrochloric acid were added in the course of one hour by the feed method. During the feed time and the subsequent boiling for four hours, the acetone formed and, to a lesser extent, hydrogen chloride and water were distilled off continuously.

In the subsequent working up, the residual amounts of hydrogen chloride and water were removed by distillation using cyclohexane as an entraining agent, the hydrochloride of 1,4-bisaminoxybutane was taken up in water and cyclohexane was separated off. The hydrochloride was obtained in a yield of 95.3%.

EXAMPLE 3

Preparation of a Substantially Salt-Free Solution of 1,4-bisaminoxybutane (Stages c and d)

The salt removal was carried out batchwise.
a) Apparatus

The apparatus consisted of an electrodialysis cell (ED cell) having three circulations (diluate, concentrate and electrode flushing circulation). Each of these circulations was equipped with a magnetic centrifugal pump, a heat exchanger and storage container and connected to the ED cell via hoses.

The ED cell had two platinum electrodes, each of which had an area of 35 cm². The electrode spaces were separated from the adjacent concentrate chambers by cation exchange membranes of the type Nafion® (DuPont). In addition, the electrode chambers were connected to the electrode flushing circulation. 11 concentrate chambers and 10 diluate chambers, arranged alternately, were present between the electrode chambers. The chambers were separated from one another alternately by cation exchange membranes of the type Selemion® CMV and anion exchange membranes of the type Selemion® (Asahi Glass). All membranes had an active area of 37 cm². The membrane spacings were 1 mm. The feed and discharge of the particular solutions were achieved through corresponding connecting holes in the sealing frames and the end plates and by the connection to the corresponding circulations.

The membranes of the Nafion type are copolymers of tetrafluoroethylene and a perfluorinated unsaturated aliphatic sulfonic acid, eg. perfluoro-3,6-dioxa-4-methyloct-7-enesulfonic acid, and the membranes of the Selemion type consist of crosslinked polystyrene which carries sulfo groups or quaternary ammonium groups as ion exchange groups.

b) Solutions

The circulations of the electrodialysis apparatus were charged with the following solutions:

Diluate: An aqueous solution of about pH 9.5 which contained 1,4-bisaminoxybutane and sodium chloride and had been obtained by neutralization of the aqueous solution of the hydrochloride of 1,4-bisaminoxybutane with sodium hydroxide solution was used. The precipitated byproducts of the cleavage of the butylene 1,4-bisacetone oxime ether were filtered off using active carbon prior to the electrodialysis.

Concentrate: 0.9–1.8 kg of demineralized water containing 0.5% by weight of sodium chloride Electrode flushing solution: 2 kg of an $Na_2SO_4$ solution having a conductivity of about 100 mS/cm.

c) Procedure

The solutions were circulated over the ED cell and electrodialysis was carried out at about 35° C. at a cell voltage of up to 30 V and with an electrodialysis current up to 3 A.

Two experiments were carried out, using 1 and kg of diluate. Diluate 1 contained 9.6% by weight of 1,4-bisaminoxybutane and 7.4% by weight of sodium chloride and diluate 2 contained 9.3% by weight of 1,4-bisaminoxybutane and 6% by weight of sodium chloride. The experiments were terminated after 140 and 260 minutes, respectively, after the amount of salt of the diluate had decreased by 95 and 97%, respectively. The losses of 1,4-bisaminoxybutane were only about 5% in both cases.

EXAMPLE 4

Preparation of a Polymer Dispersion A

The dispersion was prepared at 85° C. by adding feed 1 in the course of 180 minutes and feed 2 in the course of 210 minutes to an initially taken mixture heated beforehand for 15 minutes at 80° C., and allowing the reaction to continue for a further 60 minutes at 80° C.

Feed 1, emulsion of 340 g of demineralized water 650 g of vinyl propionate 270 g of tert-butyl acrylate 80 g of n-butyl acrylate 10 g of acrylic acid 20 g of a 50% strength by weight aqueous solution of acrylamide 80 g of a 50% strength by weight aqueous solution of diacetoneacrylamide (N-(1,1-dimethyl-3-oxo-butyl)-acrylamide)

and an emulsifier mixture of 100 g of a 20% strength by weight aqueous solution of the sodium salt of a $C_{12}$-fatty alcohol sulfate etherified with 2.5 ethylene oxide units and 75 g of a 20% strength by weight aqueous solution of a $C_{16}/C_{18}$-fatty alcohol mixture etherified with 18 ethylene oxide units.

Feed 2

100 g of demineralized water 5 g of sodium persulfate

Initially taken mixture 365 g of demineralized water 80 g of feed 1

10.5 g of feed 2

2.5 g of sodium acetate (buffer)

2 g of acrylic acid

EXAMPLE 5

Preparation of a Polymer Dispersion B

The dispersion was prepared at 85° C. by adding feed 1 in the course of 120 minutes and feed 2 in the course of 150 minutes to an initially taken mixture heated beforehand for 15 minutes at 85° C., and allowing the reaction to continue for a further 60 minutes at 85° C.

Feed 1, emulsion of 108 g of demineralized water 400 g of ethyl acrylate 90 g of methyl methacrylate and 50 g of a 20% strength by weight aqueous solution of diacetoneacrylamide (N-(1, 1-dimethyl-3-oxo-butyl)-acrylamide)

and an emulsifier mixture of 50 g of a 20% strength aqueous solution of the disodium salt of p-dodecyldiphenyl ether disulfonic acid and 50 g of a 20% strength by weight aqueous solution of a p-isononylphenol etherified with 50 ethylene oxide units.

Feed 2

100 g of demineralized water 3 g of sodium persulfate

Initially taken mixture 200 g of demineralized water 37 g of feed 1

20 g of feed 2

EXAMPLE 6

Preparation of Crosslinkable Dispersions and Films Thereof

The dispersion A according to Example 4 was brought to a solids content of 50% by weight. 9.9 g of an aqueous solution which contained 0.95 g of 1,4-bisaminoxybutane (0.7 mol/mol of carbonyl groups in the polymer) and from which salt had been removed according to Example 3 down to a residual content of about 8 mol %, based on 1,4-bisaminoxybutane, of sodium chloride were added to 100 g of this dispersion.

The ready-to-use dispersion thus obtained remained stable over an observation period of 4 days and, after application to a glass sheet at room temperature, gave a clear crosslinked film.

For comparison, the same amount of aqueous solution of 1,4-bisaminoxybutane from which however the salt had not yet been removed was added to this dispersion.

This dispersion was found to have coagulated after about one day.

The dispersion B, in which the molar ratio of the crosslinking agent to the number of carbonyl groups in the polymer was 0.5:1, exhibited similar behavior.

We claim:

1. A process for the preparation of a substantially salt-free aqueous solution of a bisaminoxyalkane (I), comprising a) reacting a dihaloalkane (II) with a ketoxime (III) in an aqueous solution of a strong mineral base to form an alkylene bisoxime ether (IV), b) cleaving the alkylene bisoxime ether (IV) with a strong mineral acid and water to form (1) a ketone and (2) salt(s) of the mineral acid and the bisaminoxyalkane (I), and then separating off the ketone, c) adding an alkali metal hydroxide to the remaining aqueous solution to react with the salt(s) of the mineral acid and the bisaminoxyalkane (I) to form the bisaminoxyalkane (I) and salt(s) of the mineral acid and the alkali metal hydroxide, and d) removing substantially all of said salt(s) from the resulting aqueous solution by electrodialysis.

2. A process as claimed in claim 1, wherein a straight-chain $\alpha,\omega$-dichloro- or $\alpha,\omega$-dibromo-$C_2$–$C_{12}$-alkane is used as dihaloalkane (II).

3. A process as claimed in claim 1, wherein acetone oxime is used as ketoxime (III) in stage (a).

4. A process as claimed in claim 1, wherein sodium hydroxide or calcium hydroxide is used as the strong mineral base in stage (a).

5. A process as claimed in claim 1, wherein hydrochloric acid is used as the strong mineral acid in stage (b).

6. The process of claim 1, wherein the reaction in step a) is carried out in the presence of a phase transfer catalyst.

7. The process of claim 1, wherein an alkylenebisacetone oxime ether is hydrolyzed with aqueous hydrochloric acid and the acetone formed is removed continuously from the reaction mixture, as step (b).

8. A process for the preparation of a substantially salt-free aqueous solution of a bisaminoxyalkane (I), wherein an aqueous solution of a bisaminoxyalkane (I), which solution contains alkali metal salts, is subjected to electrodialysis.

9. A process as claimed in claim 8, wherein electrodialysis is carried out at a pH which is equal to or greater than the pH of the salt-free aqueous solution of the bisaminoxyalkane (I).

* * * * *